US009603583B2

(12) United States Patent
Choi et al.

(10) Patent No.: US 9,603,583 B2
(45) Date of Patent: Mar. 28, 2017

(54) METHOD, APPARATUS, AND SYSTEM FOR ANALYZING ELASTOGRAPHY OF TISSUE USING ONE-DIMENSIONAL ULTRASOUND PROBE

(71) Applicant: Samsung Electronics Co., Ltd., Suwon (KR)

(72) Inventors: Ki-wan Choi, Anyang (KR); Ji-young Park, Yongin (KR); Hyoung-ki Lee, Seongnam (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 631 days.

(21) Appl. No.: 13/868,460

(22) Filed: Apr. 23, 2013

(65) Prior Publication Data
US 2014/0081135 A1    Mar. 20, 2014

(30) Foreign Application Priority Data
Sep. 17, 2012    (KR) ......................... 10-2012-0102997

(51) Int. Cl.
| | | |
|---|---|---|
| *A61B 8/08* | (2006.01) | |
| *G01S 15/89* | (2006.01) | |
| *G01S 7/52* | (2006.01) | |
| *A61B 8/00* | (2006.01) | |

(52) U.S. Cl.
CPC .......... *A61B 8/485* (2013.01); *G01S 7/52042* (2013.01); *G01S 15/8918* (2013.01); *A61B 8/4494* (2013.01); *A61B 8/5223* (2013.01)

(58) Field of Classification Search
CPC . G01S 15/8918; G01S 7/52042; A61B 8/485; A61B 8/4494; A61B 8/5223
See application file for complete search history.

(56) References Cited

U.S. PATENT DOCUMENTS

| | | | |
|---|---|---|---|
| 5,810,731 A | 9/1998 | Sarvazyan et al. | |
| 8,225,666 B2 * | 7/2012 | McAleavey | A61B 8/08 600/442 |
| 2002/0010398 A1 | 1/2002 | Bonnefous | |

(Continued)

FOREIGN PATENT DOCUMENTS

KR    10-2012-0039545    4/2012

OTHER PUBLICATIONS

Orescanin et al., "3D Shear Wave Imaging: A simulation and experimental study". 2010 IEEE International Ultrasonics Symposium Proceedings. Oct. 11-14, 2010.*

*Primary Examiner* — Long V Le
*Assistant Examiner* — Colin T Sakamoto
(74) *Attorney, Agent, or Firm* — Staas & Halsey LLP

(57) ABSTRACT

A method of analyzing elastography of tissue using a one-dimensional (1D) ultrasound probe. The method includes: acquiring two-dimensional (2D) ultrasound images with respect to a region of interest (ROI) of an object to be diagnosed, to which a shear wave is induced, using the 1D ultrasound probe; measuring a displacement of the shear wave from the acquired 2D ultrasound images; estimating a change rate in the displacement of the shear wave along a y-axis direction orthogonal to a 2D plane on which the 2D ultrasound images are shown, using the measured displacement; and analyzing elastography information of tissue in the ROI using the measured displacement and the estimated displacement change rate.

10 Claims, 10 Drawing Sheets
(5 of 10 Drawing Sheet(s) Filed in Color)

(56) References Cited

U.S. PATENT DOCUMENTS

| | | |
|---|---|---|
| 2004/0225215 A1 | 11/2004 | Querleux et al. |
| 2005/0252295 A1 | 11/2005 | Fink et al. |
| 2006/0264736 A1 | 11/2006 | Ehman et al. |
| 2009/0056453 A1* | 3/2009 | McAleavey ............ A61B 8/08 73/597 |
| 2009/0124901 A1 | 5/2009 | Fink et al. |
| 2010/0130865 A1 | 5/2010 | Sandrin et al. |
| 2010/0240994 A1 | 9/2010 | Zheng |
| 2012/0123263 A1 | 5/2012 | Osaka et al. |

* cited by examiner

METHOD, APPARATUS, AND SYSTEM FOR ANALYZING ELASTOGRAPHY OF TISSUE USING ONE-DIMENSIONAL ULTRASOUND PROBE

CROSS-REFERENCE TO RELATED APPLICATIONS

This application claims the benefit of Korean Patent Application No. 10-2012-0102997, filed on Sep. 17, 2012, in the Korean Intellectual Property Office, the disclosure of which is incorporated herein in its entirety by reference.

BACKGROUND

1. Field

The present disclosure relates to methods, apparatuses, and systems for analyzing elastography of tissue using a one-dimensional ultrasound probe.

2. Description of the Related Art

Recently, computer aided diagnosis (CAD) systems for primarily determining medical images, such as ultrasound images, magnetic resonance imaging (MRI) images, and computer tomography (CT) images, to provide the presence/absence and a location of abnormal tissue to a user have been developed. Each of the CAD systems aids a user to perform image diagnosis by detecting abnormal tissue based on the presence/absence of the abnormal tissue in medical images, a magnitude of the abnormal tissue, and a location of the abnormal tissue, which are processed by a computer system, and providing a detection result to the user and may be used together with an ultrasound apparatus, an MRI apparatus, a CT apparatus, or the like.

SUMMARY

Provided are a method, an apparatus and a system for analyzing elastography of tissue using a one-dimensional ultrasound probe.

Provided is a computer-readable recording medium storing a computer-readable program for executing the method.

Additional aspects will be set forth in part in the description which follows and, in part, will be apparent from the description, or may be learned by practice of the presented embodiments.

According to an aspect of the present disclosure, a method of analyzing elastography of tissue using a one-dimensional (1D) ultrasound probe includes: acquiring two-dimensional (2D) ultrasound images with respect to a region of interest (ROI) of an object to be diagnosed, to which a shear wave is induced, using the 1D ultrasound probe; measuring a displacement of the shear wave from the acquired 2D ultrasound images; estimating a change rate in the displacement of the shear wave along a y-axis direction orthogonal to a 2D plane on which the 2D ultrasound images are shown, using the measured displacement; and analyzing elastography information of tissue in the ROI using the measured displacement and the estimated displacement change rate.

According to another aspect of the present disclosure, provided is a computer-readable recording medium storing a computer-readable program for executing the method of analyzing elastography of tissue using a one-dimensional (1D) ultrasound probe.

According to another aspect of the present disclosure, an apparatus for analyzing elastography of tissue using a one-dimensional (1D) ultrasound probe includes: an ultrasound image processor for acquiring two-dimensional (2D) ultrasound images with respect to a region of interest (ROI) of an object to be diagnosed, to which a shear wave is induced, using the 1D ultrasound probe; a displacement measurer for measuring a displacement of the shear wave from the acquired 2D ultrasound images; a change rate information estimator for estimating a change rate in the displacement of the shear wave along a y-axis direction orthogonal to a 2D plane on which the 2D ultrasound images are shown, using the measured displacement; and an elastography analyzer for analyzing elastography information of tissue in the ROI using the measured displacement and the estimated displacement change rate.

According to another aspect of the present disclosure, an elastography analysis system includes a one-dimensional ultrasound probe and a shear wave processing apparatus. The shear wave processing apparatus includes an ultrasound image processor to acquire two-dimensional (2D) ultrasound images of a region of interest in which a shear wave is induced using the 1D ultrasound probe, a displacement measurer to measure a displacement of the shear wave by cross-correlating a plurality of sequential ultrasound images of the acquired 2D ultrasound images, a change rate information estimator to estimate a change rate in a displacement of the shear wave along a y-axis direction orthogonal to a 2D plane on which the 2D ultrasound images are shown, using the measured displacement; and an elastography analyzer to analyze elastography information of tissue in the region of interest using the measured displacement and the estimated displacement change rate.

BRIEF DESCRIPTION OF THE DRAWINGS

The patent or application file contains at least one drawing executed in color. Copies of this patent or patent application publication with color drawings will be provided by the Office upon request and payment of the necessary fee. These and/or other aspects will become apparent and more readily appreciated from the following description of the embodiments, taken in conjunction with the accompanying drawings in which.

DETAILED DESCRIPTION

Figure 1:
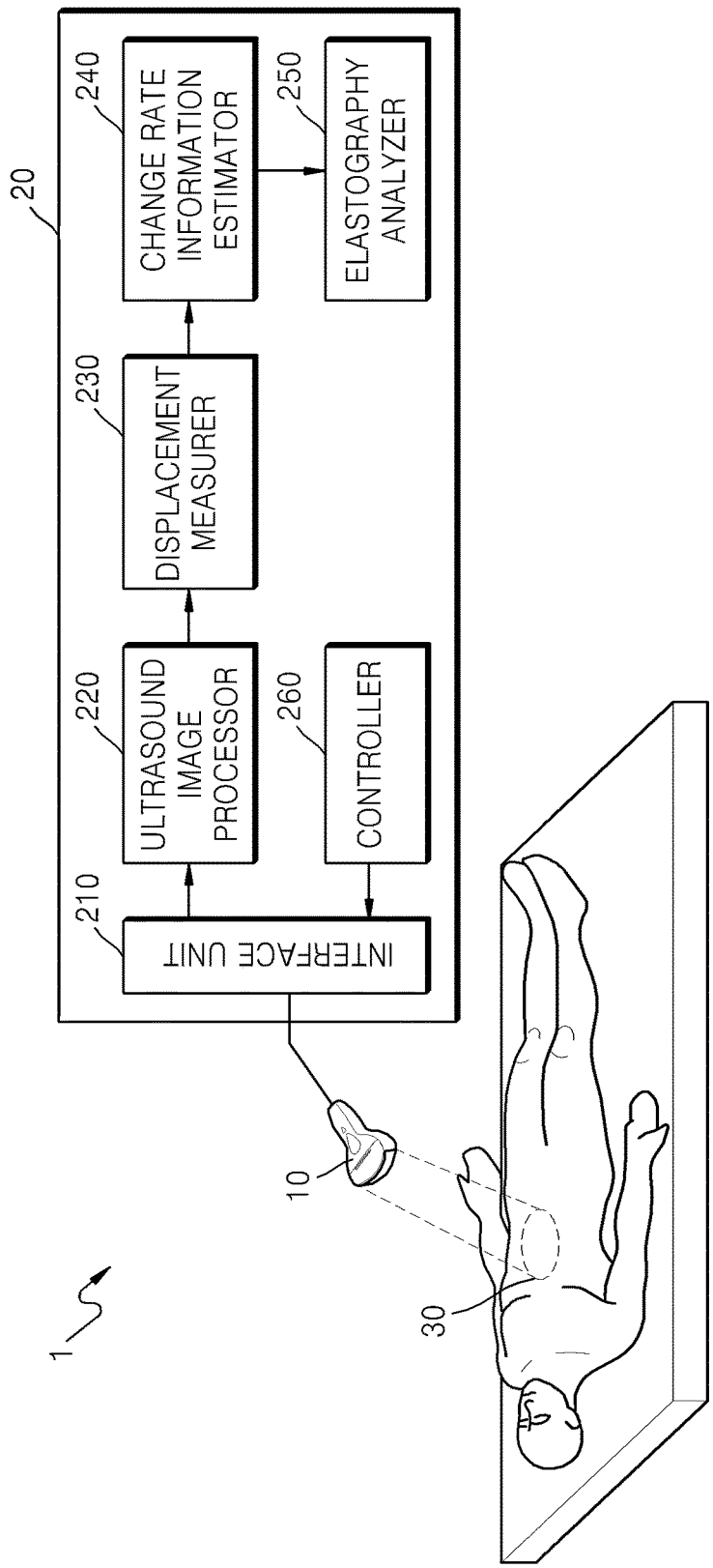
FIG. 1 is a block diagram illustrating a usage environment of an elastography analysis system according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

FIG. 1 is a block diagram illustrating a usage environment of an elastography analysis system 1 according to an embodiment of the present disclosure.

Referring to FIG. 1, the elastography analysis system 1 may include a one-dimensional (1D) ultrasound probe 10 and a shear wave processing apparatus 20. The shear wave processing apparatus 20 may include, for example, an interface unit 210, an ultrasound image processor 220, a displacement measurer 230, a change rate information estimator 240, an elastography analyzer 250, and a controller 260.

Only components related to the current embodiment are shown in the elastography analysis system 1 of FIG. 1. However, one of ordinary skill in the art understands that the elastography analysis system 1 may further include general-use components other than the components shown in FIG. 1.

In addition, the interface unit 210, the ultrasound image processor 220, the displacement measurer 230, the change rate information estimator 240, the elastography analyzer 250, and the controller 260 of the shear wave processing apparatus 20 shown in FIG. 1, may correspond to or include one or more processors. The one or more processors may be implemented by an array of a plurality of logic gates or by a combination of a general-use microprocessor and a memory storing programs executable by the microprocessor. In addition, one of ordinary skill in the art understands that the processor may be implemented by another type of hardware.

The elastography analysis system 1 may be used in a system as described below. Ultrasound elastography technology is diagnosis technology for analyzing elastography of tissue to detect a stiffness difference between normal tissue, which is tissue without tumors or cancer, and abnormal tissue. Specifically, the elastography analysis system 1 may be used to determine a state of tissue in a body, like the human body, such as whether abnormal tissue, such as cancerous tissue or tissue having a tumor exists, by analyzing elastography of the tissue using ultrasound waves. The elastography analysis system 1 may also determine whether the tissue has been completely treated when the tissue is treated using high intensity focused ultrasound (HIFU).

Alternatively, the elastography analysis system 1 may be used to detect diseased or abnormal tissue in a living animal or may be used to inspect animal tissue of a living or dead animal, such as to determine the quality of animal meat for human consumption.

In general, the stiffness of abnormal tissue is different from that of normal tissue, and the abnormal tissue may be determined by analyzing this difference. Thus, abnormal tissue, such as cancerous tissue or tissue having a tumor, may have a higher elastography value than normal tissue. Accordingly, the abnormal tissue, such as cancerous tissue or tumorous tissue, has a higher shear modulus than surrounding normal tissue. In addition, even when tissue is necrosed using ultrasound waves for treatment, such as HIFU, an elastography value of the tissue increases along with the necrosis of the tissue. That is, a change in a state of tissue may be replaced with a change in elastography of the tissue. Thus, if elastography of tissue in the human body is detected using ultrasound waves, a state of the tissue may be monitored in a non-invasive manner without a need for directly viewing the tissue.

The elastography analysis system 1 may be used to diagnose a disease, make a treatment plan, evaluate the progress of a treatment, or the like by providing a result obtained from analyzing elastography of tissue using ultrasound images. A configuration and operation of the elastography analysis system 1 will now be described in more detail.

The 1D ultrasound probe 10 induces a shear wave to a region of interest (ROI) 30 of an object to be diagnosed. The ROI 30 refers to a region that is irradiated with ultrasound waves using the 1D ultrasound probe 10. In addition, the ROI 30 may include tissue having a lesion to be treated. However, the current embodiment is not limited thereto.

For example, the 1D ultrasound probe 10 induces the shear wave in the ROI 30 by focusing an ultrasound signal at one or more points in the ROI 30 prior to analyzing elastography of tissue. To quantitatively analyze the elastography using ultrasound waves, the 1D ultrasound probe 10 may irradiate an acoustic radiation force impulse (ARFI) corresponding to an ultrasound wave of the current embodiment to the inside of the human body. In this case, a shear wave is generated in the tissue due to the irradiated ARFI, thereby resulting in a displacement of the tissue.

Figure 3A:
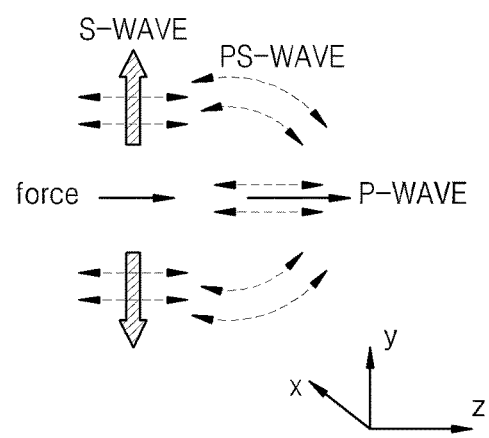
FIGS. 3A and 3B are diagrams for describing a shear wave according to an embodiment of the present disclosure.
Figure 3B:
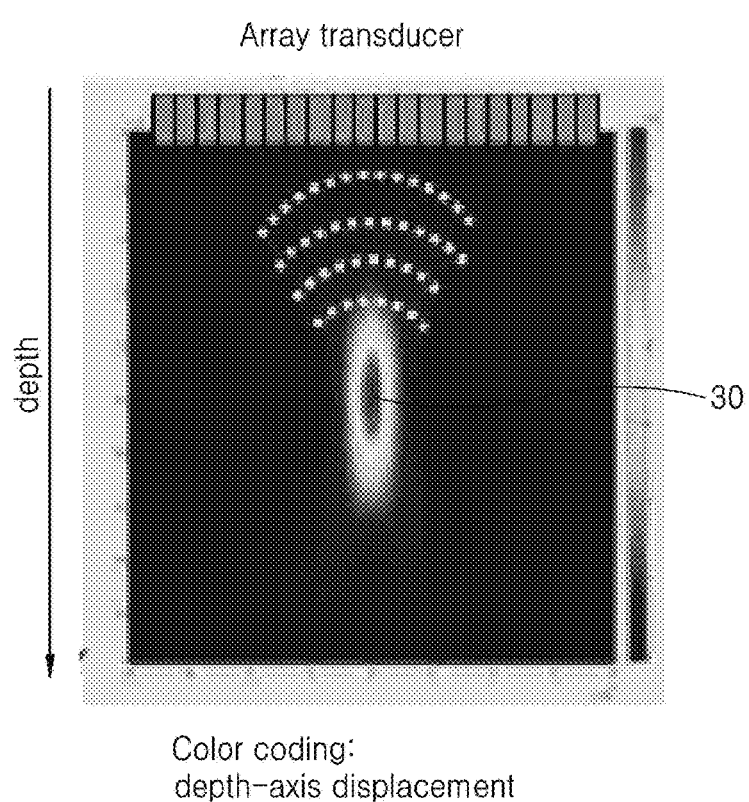

FIG. 3 is a diagram for describing a shear wave according to an embodiment of the present disclosure. Referring to FIG. 3, when a force of a point impulse is applied along a z-axis direction, a P wave that is a longitudinal wave, an S wave that is a transverse wave, and a PS wave that is a coupling wave of the P wave and the S wave are generated. The shear wave is a wave vibrating along a wave traveling direction and traveling along a y-axis direction from a vibration source to which the force is applied, i.e., the S wave.

It is described in the current embodiment, merely for convenience of description, that the ultrasound waves irradiated by the 1D ultrasound probe 10 are used for the force of the point impulse for inducing the shear wave. However, the current embodiment is not limited thereto, and a treatment ultrasound device, such as a HIFU device, or a vibrator in a magnetic resonance imaging (MRI) device, which is located external to or separate from the elastography analysis system 1 may also be used to generate the shear wave. That is, one of ordinary skill in the art understands that a device for inducing the shear wave within the ROI 30 is not limited to any one device and may include various devices.

The 1D ultrasound probe 10 radiates the ultrasound waves towards the ROI 30 and receives echo ultrasound waves reflected from the ROI 30. In a current embodiment, the ROI 30 refers to a point at which the shear wave is induced and tissue surrounding the point, that is a surrounding region. In addition, the ROI 30 is a region included in an ultrasound image acquired by the ultrasound image processor 220 using the echo ultrasound waves and may be set as a region in which an amplitude of the shear wave generated by the 1D ultrasound probe 10 is maintained greater than a certain level. For example, the ROI 30 may be set as a rectangular form, the origin of which is a first focal point, which is 2 cm wide and 2 cm long. However, the current embodiment is not limited thereto. In detail, the ROI 30 may be set as a square region, a circular region, or other polygonal regions. In addition, the ROI 30 may be set by the controller 260 by considering the amplitude of the generated shear wave without user input or may be directly set by the user via the interface unit 210.

Figure 4:
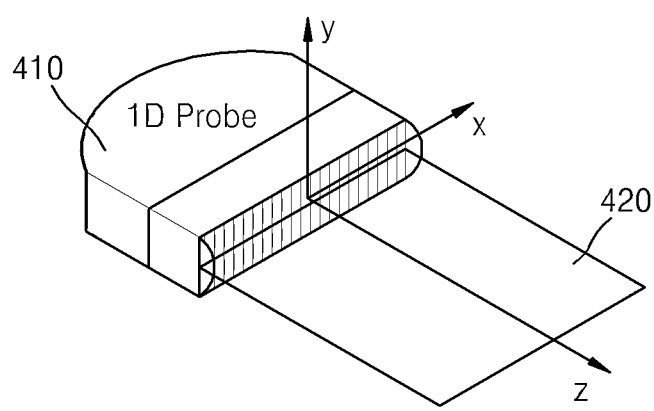
FIG. 4 is a perspective view of a 1D ultrasound probe irradiating ultrasound waves, according to an embodiment of the present disclosure.

FIG. 4 is a perspective view of a 1D ultrasound probe 410 irradiating ultrasound waves, according to an embodiment of the present disclosure.

Referring to FIG. 4, the 1D ultrasound probe 410 may include a one-dimensional (1D) array of a plurality of transducers. The transducers, which may be elements included in the 1D ultrasound probe 410, irradiate the ROI 30 with ultrasound waves and receive echo ultrasound waves reflected from the ROI 30. For example, when the transducers irradiate ultrasound signals at about 2 MHz to about 18 MHz to the ROI 30, the ultrasound signals are partially reflected from layers between various different tissues. These reflected echo signals cause the transducers to vibrate, which generate electrical pulses in response to the vibrations and output the generated electrical pulses to the interface unit 210.

In addition, the transducers included in the 1D ultrasound probe 410 may form apertures or sub-arrays. Each of the apertures indicates a set of some of the transducers included in the 1D ultrasound probe 410. However, the quantity of transducers forming an aperture is not limited, and a single transducer may form a single aperture.

The 1D ultrasound probe 410 radiates the ultrasound signals towards the ROI 30 and receives echo ultrasound waves reflected from the ROI 30. For example, the transducers included in the 1D ultrasound probe 410 may be arranged along an x-axis direction, and a traveling direction of ultrasound waves irradiated by the 1D ultrasound probe 410 may be the z-axis direction. However, the current embodiment is not limited thereto. In addition, an ultrasound region 420 formed by the ultrasound waves radiated by the 1D ultrasound probe 410 may include the entire ROI 30.

Referring back to FIG. 1, the controller 260 may generate a control signal for the 1D ultrasound probe 10 to irradiate the ROI 30 with ultrasound waves. In addition, the controller 260 may transmit the control signal to the interface unit 210.

The interface unit 210 receives echo ultrasound waves, which are signals obtained when the ultrasound waves irradiated in response to the control signal are reflected from the ROI 30. For example, the interface unit 210 transmits the control signal received from the controller 260 to the 1D ultrasound probe 10 and receives echo ultrasound waves from the 1D ultrasound probe 10. The echo ultrasound waves indicate signals obtained when the ultrasound waves radiated towards the ROI 30 by the 1D ultrasound probe 10 are reflected from the ROI 30. For example, the echo ultrasound waves may be embodied as electrical pulses generated by the transducers included in the 1D ultrasound probe 10 in response to the signals reflected from the ROI 30.

The interface unit 210 may be a unit for inputting or outputting data or a unit for transmitting information directly input by the user to other units. For example, the interface unit 210 may include input/output devices, such as a display panel, a mouse, a keyboard, a touch screen, a monitor, and a speaker, and a software module for driving the input/output devices.

The ultrasound image processor 220 acquires 2D ultrasound images with respect to the ROI 30 of the object to be diagnosed in which the shear wave is induced using a 1D ultrasound probe (such as the 1D ultrasound probe 10). For example, the ultrasound image processor 220 may receive echo ultrasound waves from the interface unit 210 and acquire 2D ultrasound images with respect to the ROI 30 of the object to be diagnosed in which the shear wave is induced using the received echo ultrasound waves. The ultrasound image processor 220 may transmit the acquired 2D ultrasound images to the displacement measurer 230.

Figure 5:
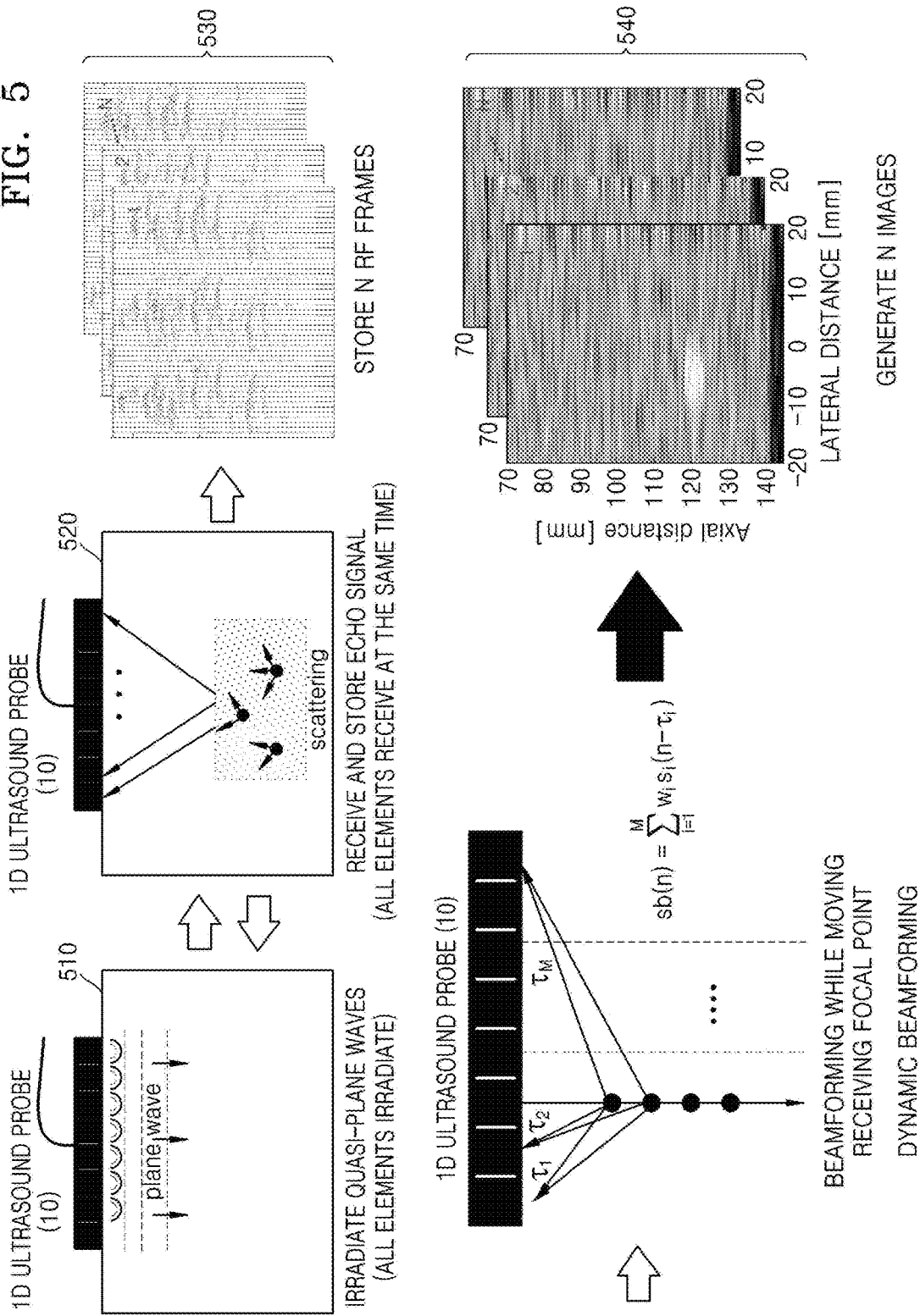
FIG. 5 illustrates a process of acquiring 2D ultrasound images with respect to an ROI in an ultrasound image processor, according to an embodiment of the present disclosure.

FIG. 5 illustrates a process of acquiring 2D ultrasound images with respect to the ROI 30 in the ultrasound image processor 220, according to an embodiment of the present disclosure.

Referring to reference numeral 510 of FIG. 5, the 1D ultrasound probe 10 irradiates the ROI 30 with ultrasound waves. For example, the 1D ultrasound probe 10 may radiate defocusing-type quasi-plane waves as the ultrasound waves with which the ROI 30 is irradiated.

Referring to reference numeral 520 of FIG. 5, the 1D ultrasound probe 10 receives echo ultrasound waves scattered and reflected from tissue in the ROI 30.

Referring to reference numeral 530 of FIG. 5, a storage unit (not shown) converts the echo ultrasound waves to digital signals and stores the digital signals as N radio frequency (RF) frames (N is a natural number). In general, a shear wave travels at a speed of about 1 m/s to about 10 m/s inside tissue of a human body. Thus, to observe the shear wave with a resolution of several mm, ultrasound waves may ideally need to be acquired in units of thousands of frames per second. To observe the shear wave at a high speed by acquiring ultrasound waves in units of thousands of frames per second, the defocusing (or unfocusing)-type quasi-plane waves described in the current embodiment are necessary as ultrasound waves for diagnosis.

Referring to reference numeral 540 of FIG. 5, the ultrasound image processor 220 generates N 2D ultrasound images by performing beamforming using the stored N RF frames.

Referring back to FIG. 1, the displacement measurer 230 measures a displacement of the shear wave from the acquired 2D ultrasound images. For example, the displacement measurer 230 may measure a displacement of the shear wave with respect to the ROI 30 from the 2D ultrasound images received from the ultrasound image processor 220. The displacement measurer 230 may transmit information about the measured displacement of the shear wave to the change rate information estimator 240.

Figure 6:
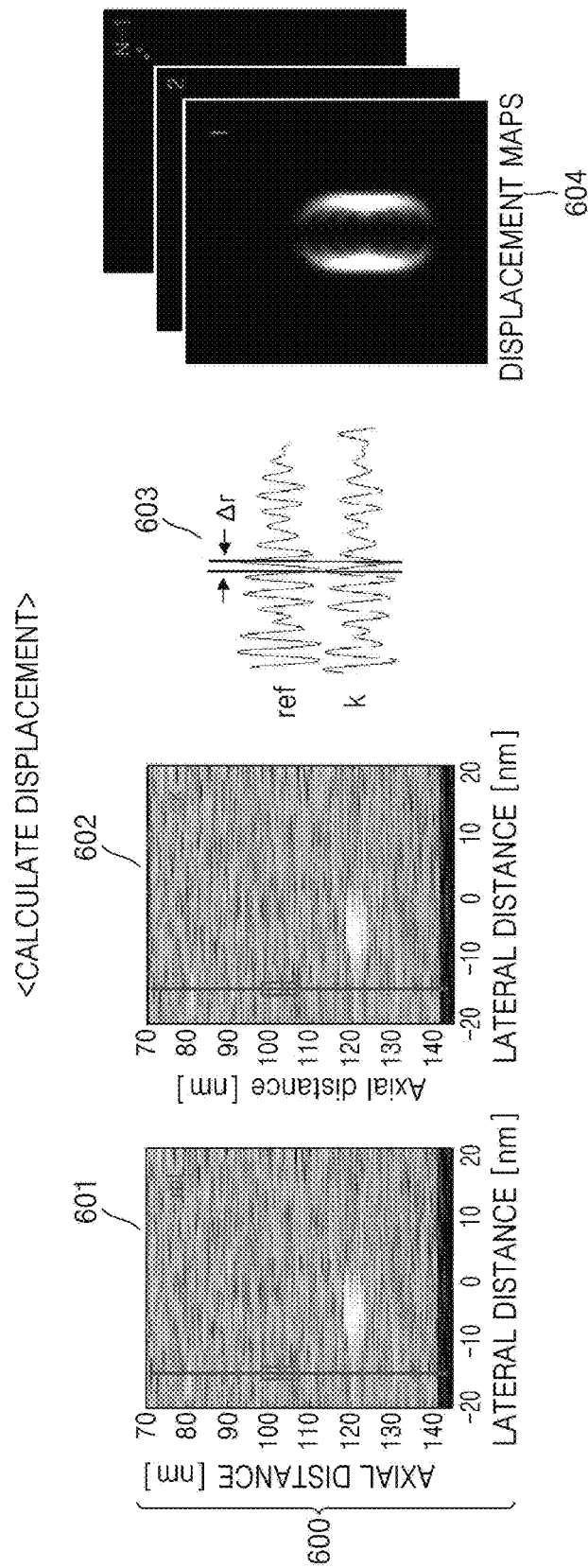
FIG. 6 illustrates a process of measuring a displacement of a shear wave in a displacement measurer, according to an embodiment of the present disclosure.

FIG. 6 illustrates a process of measuring a displacement of a shear wave in the displacement measurer 230, according to an embodiment of the present disclosure.

Referring to FIG. 6, the displacement measurer 230 cross-correlates two sequential ultrasound images 601 and 602 in operation 603. Through this cross-correlation in operation 603, the displacement measurer 230 measures a moved distance $\Delta r$ of the shear wave between the two ultrasound images 601 and 602. The displacement measurer 230 calculates a displacement u(x, z) of the shear wave using Equation 1 below, wherein the displacement u(x, z) corresponds to $g^s_{zz}$ in Equation 1.

$$g^s_{zz}(r,t) = \frac{1}{4\pi\rho c_s} \frac{1}{\sqrt{2\pi v_s t}} \frac{r^2 - z^2}{r^2} e^{-\frac{(t - r/c_s)^2 c_s^2}{2v_s t}} \quad (1)$$

In Equation 1, $g^s_{zz}$ denotes a z-axis displacement of an S-wave, ρ denotes density, $C_s$ denotes a speed of the shear wave, $v_s$ denotes a viscosity component, and r denotes a distance from the origin. Here, r corresponds to the moved distance Δr of the shear wave between the two ultrasound images 601 and 602.

Referring back to FIG. 1, the change rate information estimator 240 estimates a change rate in a displacement of the shear wave along the y-axis direction orthogonal to a 2D plane where the 2D ultrasound images are shown, using the measured displacement. The 2D plane may include the z-axis direction that is a traveling direction of the ultrasound waves irradiated by the 1D ultrasound probe 10, and the x-axis orthogonal to the z-axis direction. Although it is assumed for convenience of description in the current embodiment that the traveling direction of the ultrasound waves is the z-axis direction, embodiments are not limited thereto.

For example, the change rate information estimator 240 may calculate a change rate in a displacement of the shear wave along the x-axis direction and estimate the change rate in the displacement of the shear wave along the y-axis direction based on the calculated change rate. In detail, the change rate information estimator 240 may estimate a y-axis direction component using an x-axis direction component from a wave equation including x-, y-, and z-axes direction components of the shear wave. The change rate information estimator 240 transmits information about the change rate in the displacement of the shear wave to the elastography analyzer 250.

In general, a traveling direction of ultrasound waves radiated by the 1D ultrasound probe 10 and a displacement of a shear wave along a direction orthogonal to the traveling direction of the ultrasound waves may be measured from 2D ultrasound images acquired using the 1D ultrasound probe 10.

Referring to FIGS. 4 and 6, when it is assumed that the traveling direction of the ultrasound waves radiated by the 1D ultrasound probe 10 is the z-axis direction, the displacement measurer 230 may measure displacements of the shear wave along the z- and x-axes directions using the 2D ultrasound images but cannot measure a displacement of the shear wave along the y-axis direction.

A wave equation used to calculate a shear modulus of the shear wave induced in the ROI 30 is shown as Equation 2 below, for example.

$$\frac{\partial^2 u}{\partial t^2} = C_s^2 \cdot \left( \frac{\partial^2 u}{\partial x^2} + \frac{\partial^2 u}{\partial y^2} + \frac{\partial^2 u}{\partial z^2} \right) \quad (2)$$

In Equation 2, u denotes a displacement of a shear wave, and $C_s$ denotes a speed of the shear wave.

Since the displacement of the shear wave is measured by the displacement measurer 230 using the 2D ultrasound images, the displacement measurer 230 may measure displacements of the shear wave along the x- and z-axes directions but cannot measure a displacement of the shear wave along the y-axis direction. Thus, in general, when a displacement of the shear wave is measured using the 2D ultrasound images acquired using the 1D ultrasound probe 10, the wave equation is assumed as Equation 3 below.

$$\partial_t^2 u = C_s^2 (\partial_x^2 u + \partial_z^2 u) \quad (3)$$

As in Equation 3, when the wave equation is calculated by excluding a second-order partial differential term having a variable y as a displacement of the shear wave from Equation 2, actual elastography information of the shear wave cannot be perfectly obtained.

Thus, a process of estimating a change rate in a displacement of the shear wave along the y-axis direction (i.e., information corresponding to the term $\partial_y^{2u}$ in Equation 2) in the change rate information estimator 240 using the displacement of the shear wave, which is measured from the 2D ultrasound images, is necessary.

Figure 7:
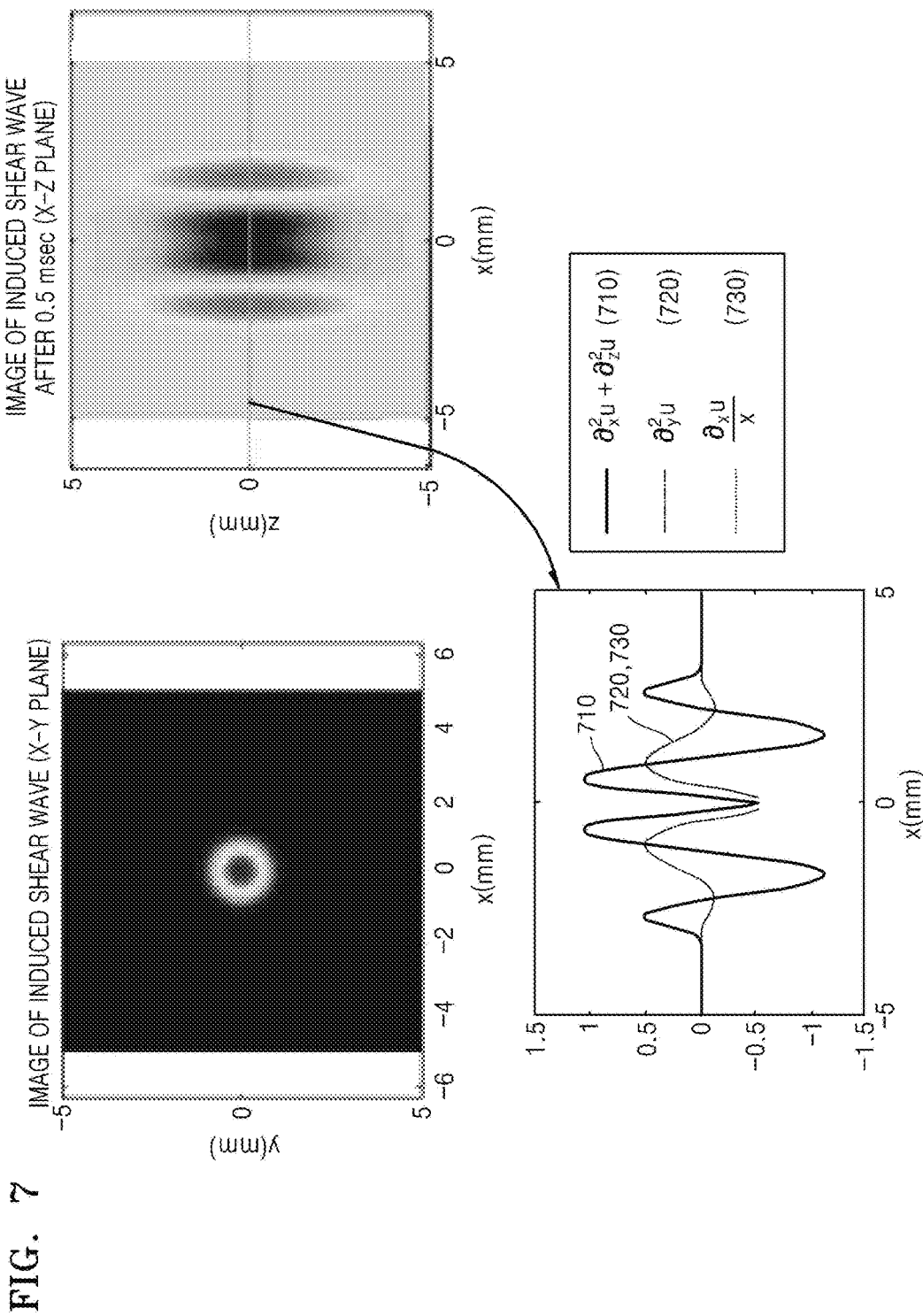
FIG. 7 illustrates 2D ultrasound images acquired using the 1D ultrasound probe and a graph of displacement components of a shear wave, according to an embodiment of the present disclosure.

FIG. 7 illustrates 2D ultrasound images acquired using the 1D ultrasound probe 10 and a graph of displacement components of a shear wave, according to an embodiment of the present disclosure.

Referring to FIG. 7, a case where a displacement of a shear wave induced in the ROI 30 is symmetric about the z-axis direction (i.e., the traveling direction of the ultrasound waves irradiated by the 1D ultrasound probe 10) is shown. In this case, as shown in the graph of FIG. 7, a curve 720 corresponding to $\partial_y^{2u}$ may have the same shape as a curve 730 corresponding to $$\frac{\partial_x u}{r}.$$

In the curve 730, x denotes a moved distance of the shear wave along the x-axis direction.

Thus, the change rate information estimator 240 may estimate a change rate in a displacement of the shear wave along the y-axis direction based on a change rate in a displacement of the shear wave along the x-axis direction. The change rate in the displacement of the shear wave along the y-axis direction indicates the second-order partial differential term $\partial_y^{2u}$ having a variable y as a displacement of the shear wave in Equation 2. In detail, the change rate information estimator 240 may estimate a change rate $\partial_y^{2u}$ in a displacement of the shear wave along the y-axis direction as $$\frac{\partial_x u}{r}$$

using the change rate $\partial_y^{2u}$ in the displacement of the shear wave along the x-axis direction and a moved distance r of the shear wave along the x-axis direction.

When the change rate information estimator 240 estimates the change rate in the displacement of the shear wave along the y-axis direction as described above, elastography information of the shear wave including 3D displacement components may be correctly analyzed from the 2D ultrasound images acquired using the 1D ultrasound probe 10. In addition, by generating an elastography image using the correctly analyzed elastography information, the elastography image may have a relatively high resolution.

Figure 8:
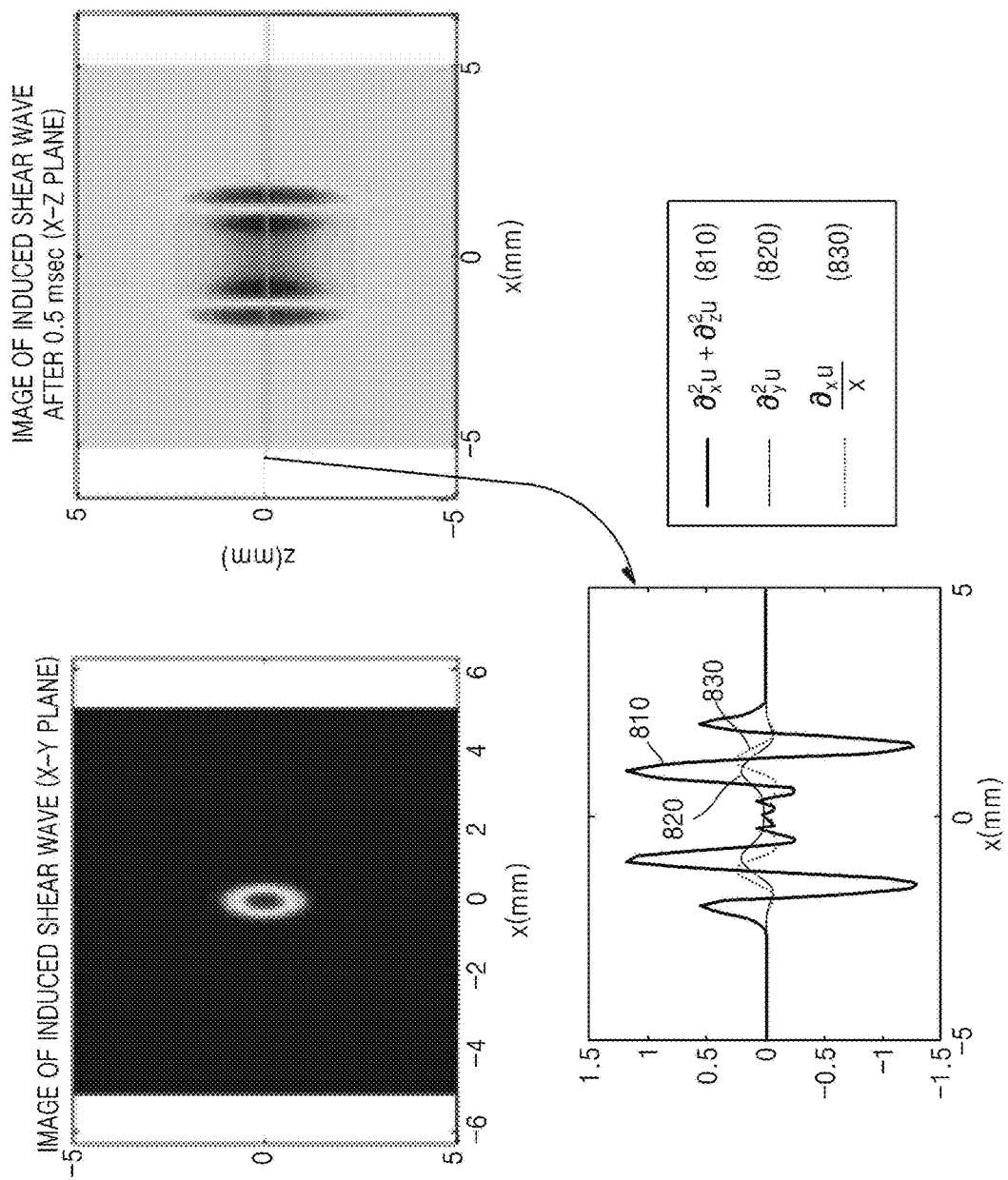
FIG. 8 illustrates 2D ultrasound images acquired using the 1D ultrasound probe and a graph of displacement components of a shear wave, according to another embodiment of the present disclosure.

FIG. 8 illustrates 2D ultrasound images acquired using the 1D ultrasound probe 10 and a graph of displacement components of a shear wave, according to another embodiment of the present disclosure.

Referring to FIG. 8, an example in which a displacement of a shear wave induced in the ROI 30 is asymmetric about the z-axis direction (i.e., the traveling direction of the ultrasound waves irradiated by the 1D ultrasound probe 10) is shown. In general, the displacement of the shear wave induced in the ROI 30 is asymmetric along the traveling direction of the ultrasound waves. In this case, as shown in the graph of FIG. 8, a curve 820 corresponding to $\partial_y^{2u}$ may not have the same shape as a curve 830 corresponding to $$\frac{\partial_x u}{r}.$$

In the curve 830, x denotes a moved distance of the shear wave along the x-axis direction.

Referring back to FIG. 1, unlike the above-described case where the displacement of the shear wave is symmetric along the x-axis direction, the change rate information estimator 240 may estimate a change rate in a displacement of the shear wave along the y-axis direction. The change rate in the displacement of the shear wave along the y-axis direction indicates the second-order partial differential term $\partial_y^2 u$ having a variable y as a displacement of the shear wave in Equation 2.

For example, the change rate information estimator 240 may calculate a y-axis direction component using the change rate in the displacement of the shear wave along the x-axis direction and the moved distance of the shear wave along the x-axis direction. The y-axis direction component is the y-axis direction component in Equation 2 and indicates the change rate in the displacement of the shear wave along the y-axis direction. In addition, the change rate information estimator 240 may calculate a y-axis direction component by additionally adjusting a scale using the calculated component. In addition, the change rate information estimator 240 may calculate a y-axis direction component by performing axis adjustment on the x-axis using the scale-adjusted component.

Figure 9:
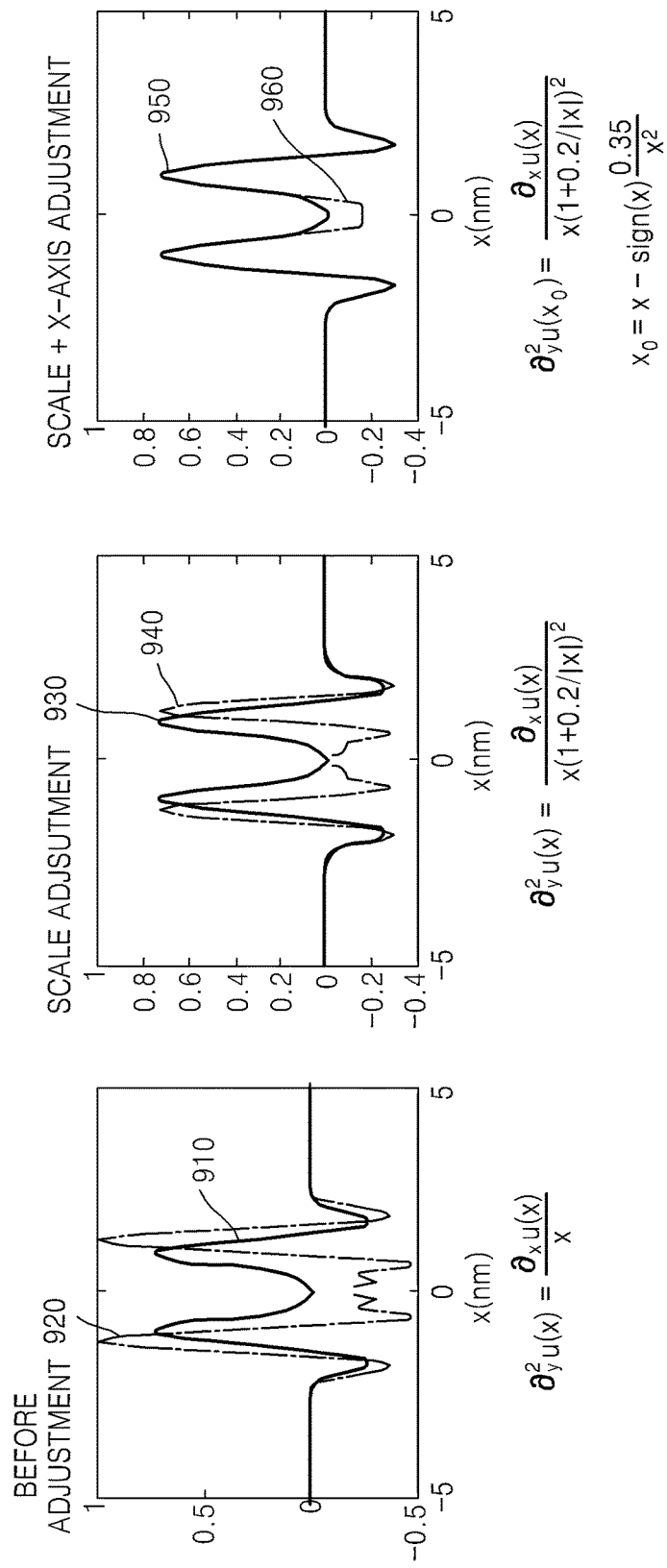
FIG. 9 illustrates examples of estimating a change rate in a displacement of a shear wave along a y-axis direction in a change rate information estimator, according to an embodiment of the present disclosure.

FIG. 9 illustrates examples of estimating a change rate in a displacement of the shear wave along the y-axis direction in the change rate information estimator 240, according to an embodiment of the present disclosure.

Referring to the left graph in FIG. 9, the change rate information estimator 240 may estimate a change rate $\partial_y^{2u}$ in a displacement of the shear wave along the y-axis direction as $$\frac{\partial_x u}{r}$$

using a change rate $\partial_y^{2u}$ in a displacement of the shear wave along the x-axis direction and a moved distance r of the shear wave along the x-axis direction.

In this case, a displacement change rate curve 920 of the shear wave along the y-axis direction, which is estimated by the change rate information estimator 240, may have a certain level of difference from an actual displacement change rate curve 910 of the shear wave along the y-axis direction. However, the change rate information estimator 240 may estimate a change rate in a displacement of the shear wave along the y-axis direction using the displacement of the shear wave, which is measured from 2D ultrasound images (i.e., ultrasound images formed with x- and z-axes direction components) through a relatively simple process.

Referring to the center graph in FIG. 9, the change rate information estimator 240 may estimate a change rate $\partial_y^{2u}$ in a displacement of the shear wave along the y-axis direction by additionally adjusting a scale using $$\frac{\partial_x u}{r}.$$

For example, the change rate information estimator 240 may calculate a change rate in a displacement of the shear wave along the y-axis direction using Equation 4 below.

$$\frac{\partial^2 u}{\partial y^2} = \frac{\partial_x u}{x(1 + 0.2/|x|)^2} \qquad (4)$$

In Equation 4, 0.2 is a constant, which may be differently set by being calibrated according to types of the 1D ultrasound probe 10 inducing the shear wave. For example, 0.2 may be a constant to which physical characteristics of the transducers included in the 1D ultrasound probe 10 are reflected.

In this case, a displacement change rate curve 940 of the shear wave along the y-axis direction, which is estimated by the change rate information estimator 240, is a result obtained by performing the scale adjustment and has a similar value to an actual displacement change rate curve 930 of the shear wave along the y-axis direction. Thus, the change rate information estimator 240 may more precisely estimate a change rate in a displacement of the shear wave along the y-axis direction using the displacement of the shear wave, which is measured from 2D ultrasound images (i.e., ultrasound images formed with x- and z-axes direction components).

Referring to the right graph in FIG. 9, the change rate information estimator 240 may estimate a change rate $\partial_y^{2u}$ in a displacement of the shear wave along the y-axis direction by additionally performing axis adjustment on the x-axis using a result obtained by calculating Equation 4 (i.e., a result obtained by performing the scale adjustment). For example, the change rate information estimator 240 may calculate a change rate in a displacement of the shear wave along the y-axis direction using Equation 5 below.

$$\frac{\partial^2 u(x_0)}{\partial y^2} = \frac{\partial_x u}{x(1 + 0.2/|x|)^2} \qquad (5)$$

$$x_0 = x - \text{sign}(x)\frac{0.35}{x^2}$$

In Equation 5, the lower equation corresponds to an example in which the axis adjustment on the x-axis is additionally performed. In Equation 5, 0.2 and 0.35 are constants to which characteristics of the 1D ultrasound probe 10 inducing the shear wave are reflected. For example, 0.2 and 0.35 may be constants to which the physical characteristics of the transducers included in the 1D ultrasound probe 10 are reflected.

In this case, a displacement change rate curve 960 of the shear wave along the y-axis direction, which is estimated by the change rate information estimator 240, is a result obtained by performing the axis adjustment on the x-axis and has a similar value to an actual displacement change rate curve 950 of the shear wave along the y-axis direction. Thus, the change rate information estimator 240 may more correctly estimate a change rate in a displacement of the shear wave along the y-axis direction using the displacement of the shear wave, which is measured from 2D ultrasound images (i.e., ultrasound images formed with x- and z-axes direction components).

Referring back to FIG. 1, the elastography analyzer 250 analyzes elastography information of tissue in the ROI 30 using the measured displacement and the estimated displacement change rate. The measured displacement indicates the displacement of the shear wave, which is measured by the displacement measurer 230 from the acquired 2D ultrasound images. In addition, the estimated displacement change rate indicates the change rate in the displacement of the shear wave along the y-axis direction, which is estimated by the change rate information estimator 240 using the measured displacement. For example, the elastography analyzer 250 may analyze the elastography information by calculating a shear modulus of the tissue in the ROI 30 using the measured displacement and the estimated displacement change rate.

In detail, the elastography analyzer 250 may analyze the elastography information by calculating the wave equation (i.e., Equation 2) including the x-, y-, and z-axes direction components of the shear wave. The y-axis direction component indicates a component calculated by the change rate information estimator 240 using the x-axis direction component. For example, the elastography analyzer 250 may calculate $C_s^2$ using Equation 2. The elastography analyzer 250 may calculate the shear modulus using Equation 6 below.

$$G = \rho \times C_s^2 \qquad (6)$$

In Equation 6, G denotes a shear modulus and $\rho$ denotes density of a medium. Previously, the elastography analyzer 250 calculated a moving speed $C_s$ of shear wave using Equation 2, and $\rho$ is an already known value, and thus, the elastography analyzer 250 may calculate the shear modulus G using Equation 6. Although it is described in the current embodiment that the elastography analyzer 250 calculates the shear modulus G using Equation 6, the current embodiment is not limited thereto.

If the elastography analyzer 250 analyzes shear moduli in units of at least two frames among the 2D ultrasound images, the elastography analyzer 250 may calculate a final shear modulus by calculating a mean value of individually calculated shear moduli.

In addition, the elastography analyzer 250 may calculate the shear modulus G using Equation 7.

$$\rho \frac{\partial^2 u_z}{\partial t^2} = G(x, y, z) \left( \frac{\partial^2 u_z}{\partial x^2} + \frac{\partial^2 u_z}{\partial y^2} + \frac{\partial^2 u_z}{\partial z^2} \right) \qquad (7)$$

$$\Leftrightarrow G(x, y, z) = \frac{\rho \frac{\partial^2 u_z}{\partial t^2}}{\frac{\partial^2 u_z}{\partial x^2} + \frac{\partial^2 u_z}{\partial y^2} + \frac{\partial^2 u_z}{\partial z^2}}$$

That is, the elastography analyzer 250 may calculate the shear modulus G using Equation 7 obtained by combining Equations 2 and 6.

As described above, by estimating 3D displacement components of the shear wave in the change rate information estimator 240 using the 2D ultrasound images, the elastography analyzer 250 may correctly analyze elastography information.

Figure 2:
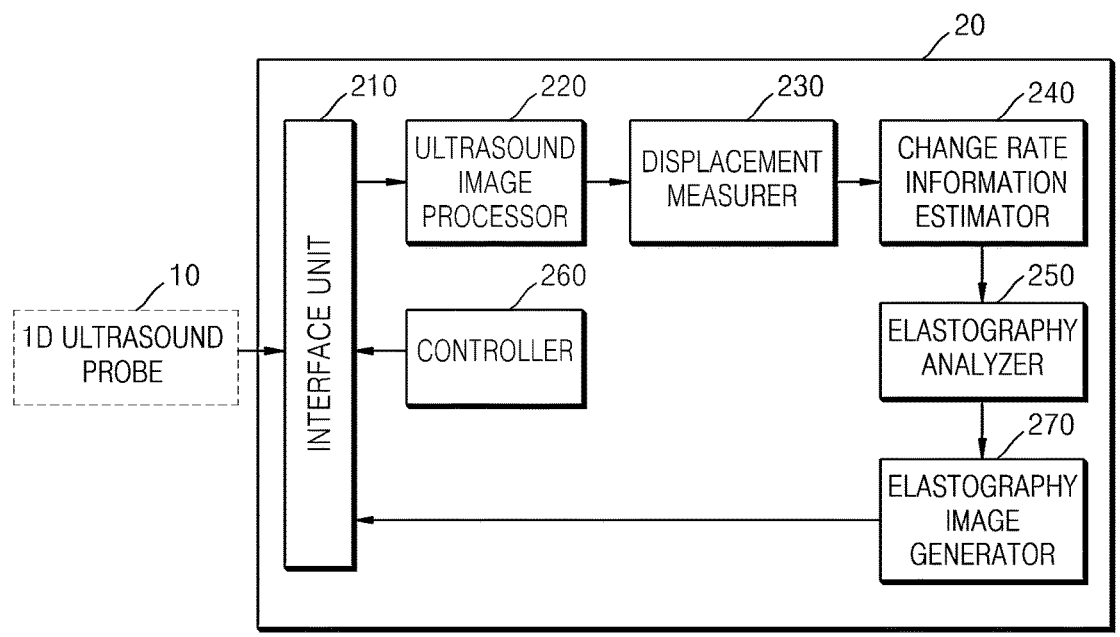
FIG. 2 is a block diagram illustrating a usage environment of an elastography analysis system according to another embodiment of the present disclosure.

FIG. 2 is a block diagram of the shear wave processing apparatus 20 according to another embodiment of the present disclosure.

Referring to FIG. 2, the shear wave processing apparatus 20 may include the interface unit 210, the ultrasound image processor 220, the displacement measurer 230, the change rate information estimator 240, the elastography analyzer 250, the controller 260, and an elastography image generator 270.

Only components related to the current embodiment are shown in the shear wave processing apparatus 20 of FIG. 2. Accordingly, one of ordinary skill in the art understands that the shear wave processing apparatus 20 may further include general-use components other than the components shown in FIG. 2.

In addition, the interface unit 210, the ultrasound image processor 220, the displacement measurer 230, the change rate information estimator 240, the elastography analyzer 250, the controller 260, and the elastography image generator 270 of the shear wave processing apparatus 20 shown in FIG. 2 may correspond to one or more processors. The one or more processors may be implemented by an array of a plurality of logic gates or by a combination of a general-use microprocessor and a memory storing programs executable by the microprocessor. In addition, one of ordinary skill in the art understands that the processor may be implemented by another type of hardware.

In addition, operations of the interface unit 210, the ultrasound image processor 220, the displacement measurer 230, the change rate information estimator 240, the elastography analyzer 250, and the controller 260, of the shear wave processing apparatus 20 shown in FIG. 2 are as described above.

The elastography image generator 270 generates an image with respect to a shear modulus of the ROI 30 using a calculated shear modulus. For example, the elastography image generator 270 may generate the image with respect to the shear modulus of the ROI 30 using information about a shear modulus received from the elastography analyzer 250. The image with respect to the shear modulus may be an image in which a displacement of a shear wave, which is changed along time, is represented with a color difference or a brightness difference. Since a general process related to the shear modulus in the elastography image generator 270 is obvious to those of ordinary skill in the art, a detailed description of an algorithm thereof is omitted.

Figure 10:
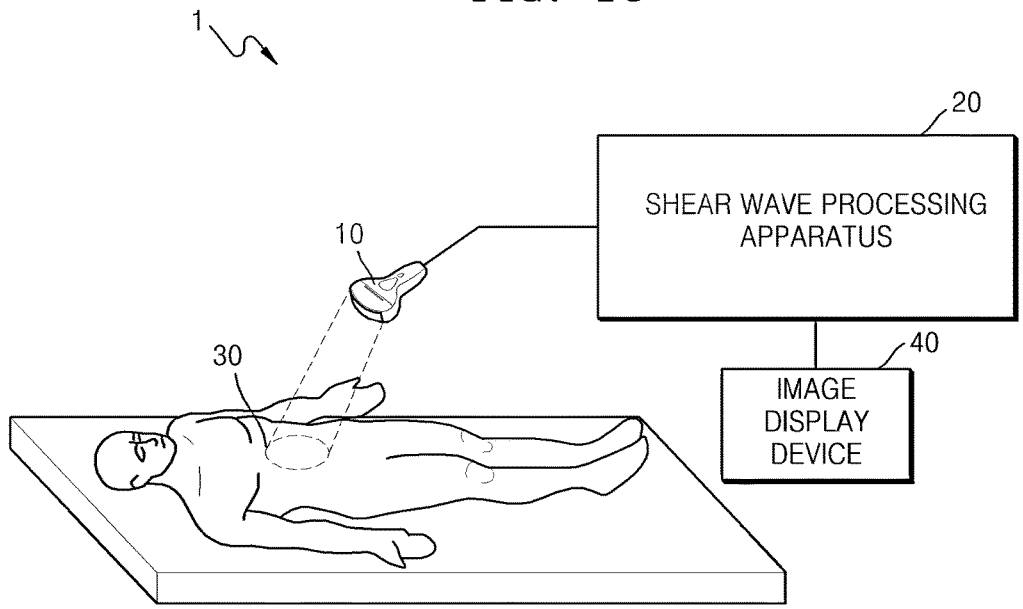
FIG. 10 is a block diagram illustrating a usage environment of an elastography analysis system according to another embodiment of the present disclosure.

FIG. 10 is a block diagram illustrating a usage environment of the elastography analysis system 1 according to another embodiment of the present disclosure. The elastography analysis system 1 of FIG. 10 may include the 1D ultrasound probe 10, the shear wave processing apparatus 20, and an image display device 40.

Only components related to the current embodiment are shown in the elastography analysis system 1 of FIG. 10. Accordingly, one of ordinary skill in the art understands that the elastography analysis system 1 may further include general-use components other than the components shown in FIG. 10.

In addition, the elastography analysis system 1 of FIG. 10 corresponds to an embodiment of the shear wave processing apparatus 20 shown in FIG. 1 or 2. Accordingly, since the descriptions with reference to FIGS. 1 and 2 are also applicable to the elastography analysis system 1 of FIG. 10, a repeated description is omitted.

The image display device 40 displays ultrasound images generated by the shear wave processing apparatus 20. For example, the image display device 40 in the elastography analysis system 1 may include any type of output device, such as a display panel, a liquid crystal display (LCD) screen, and a monitor. Elastography information, such as a shear modulus, analyzed by the shear wave processing apparatus 20 may be provided to a user through the image display device 40 so that a change in a state of tissue or characteristics of the tissue may be detected.

Figure 11:
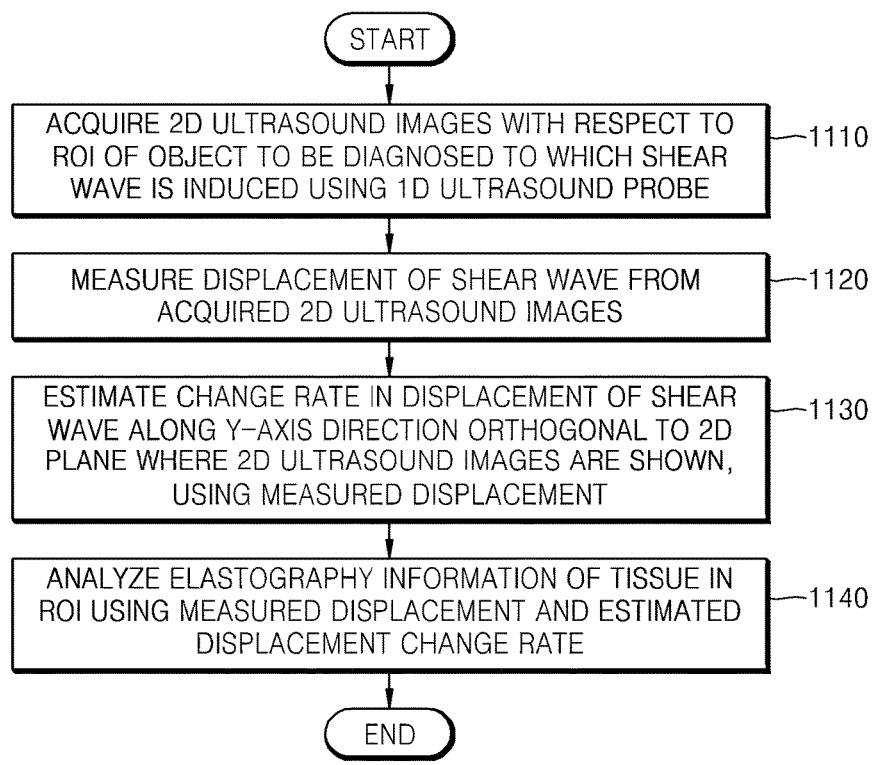
FIG. 11 is a flowchart illustrating a method of analyzing elastography information of an ROI in a shear wave processing apparatus, according to an embodiment of the present disclosure.

FIG. 11 illustrates a method of analyzing elastography information of an ROI in a shear wave processing apparatus, according to an embodiment of the present disclosure. Referring to FIG. 11, the method may include sequential operations performed by the shear wave processing apparatus 20 or the elastography analysis system 1 shown in FIG. 1, 2, or 10, or performed by other equivalent apparatuses. Thus, although omitted hereinafter, the above descriptions related to the shear wave processing apparatus 20 or the elastography analysis system 1 shown in FIG. 1, 2, or 10 are also applicable to the method of FIG. 11.

In operation 1110, the ultrasound image processor 220 acquires 2D ultrasound images of the ROI 30 of the object to be diagnosed in which a shear wave has been induced using a 1D ultrasound probe (the 1D ultrasound probe 10). The ROI 30 indicates a region which is irradiated with ultrasound waves radiated by the 1D ultrasound probe. In addition, the ROI 30 may include lesion tissue to be treated. However, the current embodiment is not limited thereto.

In operation 1120, the displacement measurer 230 measures a displacement of the shear wave from the acquired 2D ultrasound images. For example, the displacement measurer 230 may measure a moved distance of the shear wave between two sequential ultrasound images by cross-correlating the two sequential ultrasound images.

In operation 1130, the change rate information estimator 240 estimates a change rate in a displacement of the shear wave along the y-axis direction orthogonal to a 2D plane where the 2D ultrasound images are shown, using the measured displacement. For example, the change rate information estimator 240 may calculate a change rate in a displacement of the shear wave along the x-axis direction, which is included in the 2D ultrasound images, and may estimate the change rate in the displacement of the shear wave along the y-axis direction based on the calculated change rate.

In operation 1140, the elastography analyzer 250 analyzes elastography information of tissue in the ROI 30 using the measured displacement and the estimated displacement change rate.

As described above, according to the one or more of the above embodiments of the present disclosure, by estimating a change rate in a displacement of a shear wave along the y-axis direction based on a 2D plane where 2D ultrasound images are shown, using the displacement of the shear wave, which is measured by the change rate information estimator 240 from the 2D ultrasound images, elastography information of the shear wave induced in an ROI may be correctly analyzed regardless of types of ultrasound probes. In addition, the resolution of an elastography image indicating a displacement of the shear wave, which is measured using an ultrasound probe having a 1D transducer array, may be improved.

A structure of data used in the method described above may be recorded in a computer-readable recording medium by several means. The computer-readable recording medium includes storage media, such as magnetic storage media (e.g., ROM, RAM, USB, floppy disks, hard disks, etc.), optical recording media (e.g., CD-ROMs, DVDs, etc.), and PC interfaces (e.g., PCI, PCI-express, Wi-Fi, etc.).

In addition, other embodiments of the present disclosure can also be implemented through computer-readable code/instructions in/on a medium, e.g., a computer-readable recording medium, to control at least one processing element to implement any of the above-described embodiments. The computer-readable recording medium can correspond to any medium/media permitting the storage and/or transmission of the computer-readable code.

The computer-readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure including or carrying a signal or information, such as a device carrying a bitstream according to one or more embodiments of the present disclosure. The media may also be a distributed network, so that the computer-readable code is stored/transferred and executed in a distributed fashion. Furthermore, the processing element could include a processor or a computer processor, and processing elements may be distributed and/or included in a single device.

The described hardware devices may be configured to act as one or more software modules in order to perform the operations of the above-described embodiments, or vice versa. Any one or more of the software modules described herein may be executed by a controller such as a dedicated processor unique to that unit or by a processor common to one or more of the modules. The described methods may be executed on a general purpose computer or processor or may be executed on a particular machine such as the apparatus for analyzing elastography of tissue described herein.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. An apparatus for analyzing elastography of tissue using a one-dimensional (1D) ultrasound probe with transducers arranged along a single dimension, the apparatus comprising:
   an ultrasound image processor for acquiring two-dimensional (2D) ultrasound images with respect to a region of interest (ROI), of an object to be diagnosed, in which an asymmetric shear wave is induced using the 1D ultrasound probe; and
   a processor configured to:
      measure a displacement of the asymmetric shear wave from the acquired 2D ultrasound images;
      estimate a change rate in the displacement of the asymmetric shear wave along a y-axis direction orthogonal to a 2D plane in which the 2D ultrasound images acquired by the ultrasound image processor are shown, using the measured displacement;
      analyze elastography information of tissue in the ROI using the measured displacement and the estimated displacement change rate;
      generate an elastography image of the ROI using the elastography information; and
      control a display to display the elastography image.

2. The apparatus of claim 1, wherein the 2D plane includes a z-axis direction, which is a traveling direction of ultrasound waves irradiated by the 1D ultrasound probe, and an x-axis direction orthogonal to the z-axis direction.

3. The apparatus of claim 1, wherein the change rate information estimator calculates a change rate in a displacement of the asymmetric shear wave along an x-axis direction orthogonal to a z-axis direction that is a traveling direction of ultrasound waves irradiated by the 1D ultrasound probe and estimates the change rate in the displacement of the asymmetric shear wave along a y-axis direction based on the calculated change rate in the displacement of the shear wave along the x-axis direction.

4. The apparatus of claim 1, wherein the elastography analyzer analyzes the elastography information by calculating a shear modulus of tissue in the ROI using the measured displacement and the estimated displacement change rate.

5. The apparatus of claim 1, wherein the change rate information estimator estimates a y-axis direction component of the asymmetric shear wave using an x-axis direction component of the asymmetric shear wave from a wave equation including x-, y-, and z-axes direction components of the asymmetric shear wave.

6. The apparatus of claim 5, wherein the y-axis direction component is calculated using at least one of a change rate in a displacement of the asymmetric shear wave along an x-axis direction and a distance in the x-axis direction from a location at which the asymmetric shear wave is induced.

7. The apparatus of claim 6, wherein the y-axis direction component is a result obtained by adjusting a scale using the calculated component.

8. The apparatus of claim 7, wherein the y-axis direction component is a result obtained by performing axis adjustment of the x-axis direction using the scale adjustment result.

9. The apparatus of claim 4, wherein the elastography image of the ROI is generated using the calculated shear modulus.

10. An elastography analysis system comprising:
a one-dimensional (1D) ultrasound probe with transducers arranged along a single dimension; and
a shear wave processing apparatus comprising:
an ultrasound image processor to acquire two-dimensional (2D) ultrasound images of a region of interest in which a symmetric shear wave is induced using the 1D ultrasound probe; and
a processor configured to:
measure a displacement of the symmetric shear wave by cross-correlating a plurality of sequential ultrasound images of the acquired 2D ultrasound images;
estimate a change rate in a displacement of the symmetric shear wave along a y-axis direction orthogonal to a 2D plane on which the 2D ultrasound images are shown, using the measured displacement;
analyze elastography information of tissue in the region of interest using the measured displacement and the estimated displacement change rate;
generate an elastography image of the ROI using the elastography information; and
control a display to display the elastography image.

* * * * *